（12）United States Patent
Lin (10) Patent No.: US 12,296,145 B1
(45) Date of Patent: May 13, 2025

(54) SAFETY INFUSION PORT NEEDLE APPARATUS

(71) Applicant: Ming Lin, Irvine, CA (US)

(72) Inventor: Ming Lin, Irvine, CA (US)

( * ) Notice: Subject to any disclaimer, the term of this patent is extended or adjusted under 35 U.S.C. 154(b) by 0 days.

(21) Appl. No.: 18/815,986

(22) Filed: Aug. 27, 2024

(51) Int. Cl.
*A61M 5/158* (2006.01)

(52) U.S. Cl.
CPC .................. *A61M 5/158* (2013.01)

(58) Field of Classification Search
CPC .......... A61M 5/158; A61M 2005/1586; A61M 2005/1581; A61M 39/02; A61M 5/3205; A61M 5/321; A61M 5/3213
See application file for complete search history.

(56) References Cited

U.S. PATENT DOCUMENTS

| | | | | |
|---|---|---|---|---|
| 2006/0064061 | A1* | 3/2006 | Solomon | A61M 5/158 604/110 |
| 2013/0172826 | A1* | 7/2013 | Morita | A61M 5/158 604/263 |
| 2016/0074596 | A1* | 3/2016 | Mantsch | A61M 25/0625 604/263 |
| 2017/0266392 | A1* | 9/2017 | Shimer | A61M 5/3221 |
| 2021/0353876 | A1* | 11/2021 | Limaye | A61M 5/346 |

* cited by examiner

*Primary Examiner* — Michael J Tsai
*Assistant Examiner* — Neeraja Gollamudi
(74) *Attorney, Agent, or Firm* — David & Raymond Patent Firm; Raymond Y Chan (57) ABSTRACT

A safety infusion port needle apparatus includes a needle base, a port needle extended from a needle connecting portion of the needle base, a medical tubing connected to a tubing connecting portion of the needle base, a handle assembly positioned adjacent to the tubing connecting portion, a needle protector housing including two enclosure petals pivotally coupled with the needle base, and a guiding driver including a guiding sleeve portion and two supporter arm portions symmetrically extended from two opposing sides of the guiding sleeve portion respectively. When the port needle is driven by the handle assembly to pull out from the access port and body surface of the patent, two enclosure petals are driven by the guiding driver to form a tubular housing to enclose and conceal the withdrawn port needle therein.

20 Claims, 9 Drawing Sheets

FIG. 1

PRIOR ART

FIG. 2A

PRIOR ART

FIG. 2B

PRIOR ART

SAFETY INFUSION PORT NEEDLE APPARATUS

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to infusion port needle, and more particular to a safety infusion port needle apparatus configured to not only guiding the inserting and withdrawal of the port needle with respect to a body surface of a patient, but also enclosing and concealing the port needle pulled out from the body surface of the patient during withdrawal from an insertion site to prevent hazardous exposure of the medical port needle.

Description of Related Arts

A port needle is a medical device used to access implanted ports for treatments like chemotherapy. It is a thin, hollow needle that punctures the port's silicone septum, providing a pathway for medications or fluids to be administered directly into the bloodstream.

In particular, the infusion port is a relatively new implantable medication delivery device, which establishes an infusion channel that can infuse medication or nutrients into the patient's veins, arteries, abdominal cavity or spine for a long time, up to one week, through the infusion port and catheter set that is pre-implanted under the patient's skin, making the difficult and risky repeated arteriovenous, thoracic and abdominal cavity and or spinal puncture and catheter infusion into a simple subcutaneous puncture and targeted guided infusion. Also, an access port typically positioned in a body surface of a patient provides a temporary site to facilitate disposition of a catheter into a blood vessel for repeated fluid removal, infusion of medication or fluid.

Although the access port generally includes a silicon septum positioned under the skin surface of the patient to receive the port needle punctured at the insertion site and facilitate needle penetration and cover an inner chamber for the infusion of medication or removal of body fluids, in practical applications, while puncturing the needle, the tip of the needle may cause cutting damage to the injection plug of the infusion box, which may cause debris to enter the human vein or internal organs, causing thrombosis or granulomas. Also, any leaking of the infusion cartridges may cause tissue inflammation, ulceration and even necrosis. In addition, the puncture of the needle must be operated precisely to avoid injury to the body tissue or blood vessel under the body skin of the patient. The tip of the port needle withdrawn from the body surface of the patient after the infusion is exposed outside that can easily puncture the body of the operator or subsequent processor and lead to accidental infection, for example the U.S. application Ser. No. 11/380,621, filed Apr. 27, 2006.

Figure 1:
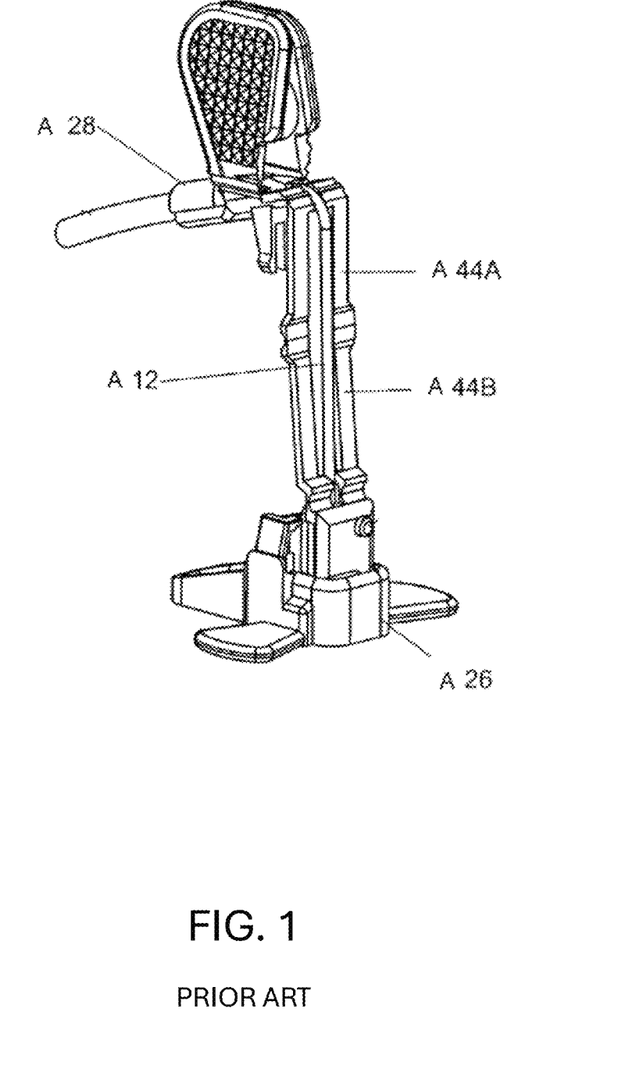
FIG. 1 is a perspective view of a conventional safety shield for medical needle.

Referring to FIG. 1, U.S. Pat. No. 7,758,544, published Mar. 23, 2006, discloses a safety shield for medical needle that is extensible to prevent hazardous exposure to a medical needle. However, the withdrawn needle A12 is not actually enclosed and concealed from outside, wherein most of the needle A12 is still exposed to outside between the extended hinged portions A44A, A44B. In addition, the unfolding of the pair of hinged portions A44A, A44B to their fully extension positions also form an obstacle mechanism between the outer bearing A26 and the hub A28 that may result in accidental injury to the body tissue or blood vessel of the patient while pulling out the needle A12 from the patient's body.

Figure 2A:
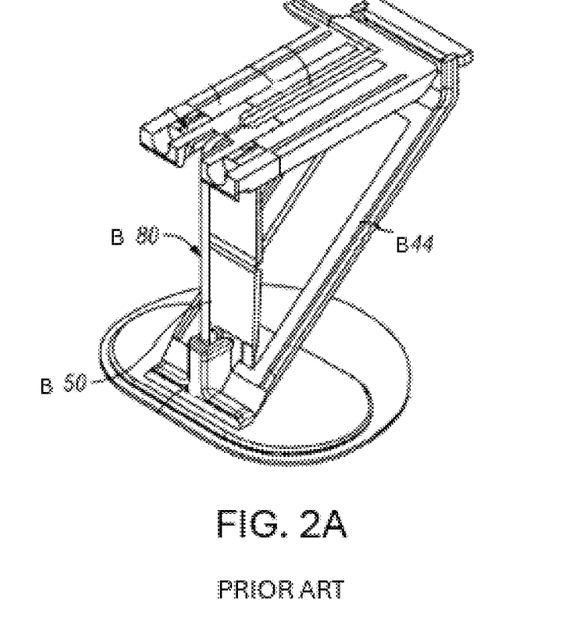
FIG. 2A and FIG. 2B are perspective views of a conventional needle assembly.
Figure 2B:
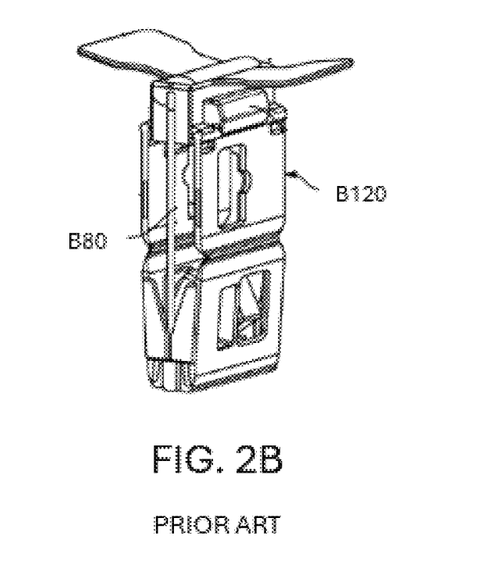

Referring to FIG. 2A and FIG. 2B, U.S. Pat. No. 7,351,230, published Nov. 30, 2006, teaches a needle assembly including a positive flush mechanism for use with a vascular access port, which is configured to supply fluid to the port and to provide a positive flush to overcome negative pressures in the port that can potentially occur during withdrawal of the needle from the port. Similarly, the withdrawn needle B80 is not actually enclosed and concealed from outside, wherein most of the needle B80 is still exposed to outside in front of the extended arm B44 and hinge B50 (as shown in FIG. 2A) or between the lower portions B120 of the needle housing (as shown in FIG. 2B). In addition, the unfolding of arm B44 and hinge B50 or of the pair of lower portions B120 of the needle housing to their fully extension positions also form an obstacle mechanism that may result in accidental injury to the body tissue or blood vessel of the patient while pulling out the needle B80 from the patient's body.

SUMMARY OF THE PRESENT INVENTION

The invention is advantageous in that it provides a safety infusion port needle apparatus, which incudes a needle base, a port needle formed from a cannula and extended from a needle connecting portion of the needle base, a medical tubing connected to a tubing connecting portion of the needle base and communicated with the port needle, a handle assembly mounted to the medical tubing and positioned adjacent to the tubing connecting portion of the needle base, a needle protector housing including two enclosure petals pivotally coupled with the needle base and configured to be moved between an operation state that the port needle is exposed for infusion operation and an enclosure state that the two enclosure petals are combined together to form a tubular housing to enclose and conceal the port needle therein, and a guiding driver comprising a guiding sleeve portion and two supporter arm portions symmetrically extended from two opposing sides of the guiding sleeve portion respectively, wherein the guiding sleeve portion is slidably set on the needle base during the operation state where the needle protector housing is positioned below the guiding driver such that the port needle is able to be inserted and implanted in an access port positioned in a body surface of a patient, and that the guiding sleeve portion is configured to be moved away from the needle base along the port needle, when the port needle is driven by the handle assembly to pull out from the access port and body surface of the patent, to drive the two enclosure petals to combine together to form the tubular housing to enclose and conceal the withdrawn port needle therein, so as to fully protect the withdrawn port needle after infusion from being contacted with outside.

Another advantage of the invention is to provide a safety infusion port needle apparatus, wherein, during the operation state, the handle assembly, the needle protector housing and the guiding driver are arranged sidewards to ensure the operator of the safety infusion port needle apparatus can access the entire port needle for precise insertion with respect to the body surface of the patient.

Another advantage of the invention is to provide a safety infusion port needle apparatus, wherein the two supporter arm portions of the guiding driver not only reinforce the positioning of the guiding sleeve portion, but also provides a stabilizing platform for the operator to stabilize a relative position of the port needle with respect to the access port and the body surface of the patient, such that when the operator applies a pulling force to the handle assembly to withdraw the port needle, the operator is able to also apply a supporting force in an opposite direction on the two supporter arm portions. Therefore, the guiding sleeve portion correspondingly guides the two enclosure petals of the needle protector housing to move towards each other until being combined to form the tubular housing while the needle base is pulling away from the guiding driver, wherein the combining and forming of the tubular housing of the two enclosure petals by means of the guiding sleeve portion of the guiding driver also significantly guide the withdrawal of the port needle in a stable and precise manner to prevent accidently injury to the body tissue or vessel of the patient during the withdrawal of the port needle.

Additional advantages and features of the invention will become apparent from the description which follows and may be realized by means of the instrumentalities and combinations particular point out in the appended claims.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

In the description of the present invention, unless explicitly stated otherwise and qualified, terms such as "connected," "attached," and "fixed" should be construed broadly. For instance, these terms may indicate a permanent connection or a detachable one, or they may refer to a whole unit. They can signify a mechanical linkage, an electrical connection, direct coupling, or indirect interaction through an intermediary medium. Whether these terms imply an internal connection between two elements or an interactive relationship between them will depend on the specific context and the understanding of those skilled in the art.

Throughout this invention, unless explicitly stated otherwise and qualified, when the first feature is described as being "above" or "below" the second feature, this may entail direct physical contact between the two features. Alternatively, it may signify that the first and second features are not in direct contact but are linked through the involvement of additional features. Additionally, the description of the first feature being "above," "over," or "on top of" the second feature includes scenarios where the first feature is positioned directly above or diagonally above the second feature or simply means that the first feature is situated at a higher horizontal level than the second feature. Conversely, when the first feature is referred to as "below," "under," or "beneath" the second feature, it encompasses cases where the first feature is directly below or diagonally below the second feature or simply implies that the first feature's horizontal height is less than that of the second feature.

In this embodiment's description, terms such as "up," "down," "right," and "left" are used to describe orientations or positional relationships. These descriptions are based on the orientations or positions depicted in the drawings and are employed for ease of explanation and simplification of operation. They should not be construed as indications or implications that the device or element being discussed must possess a specific orientation, be constructed in a particular manner, or operate exclusively in a certain orientation. Furthermore, terms such as "first" and "second" are employed solely for the purpose of distinction in the description and do not carry any particular significance.

Figure 3:
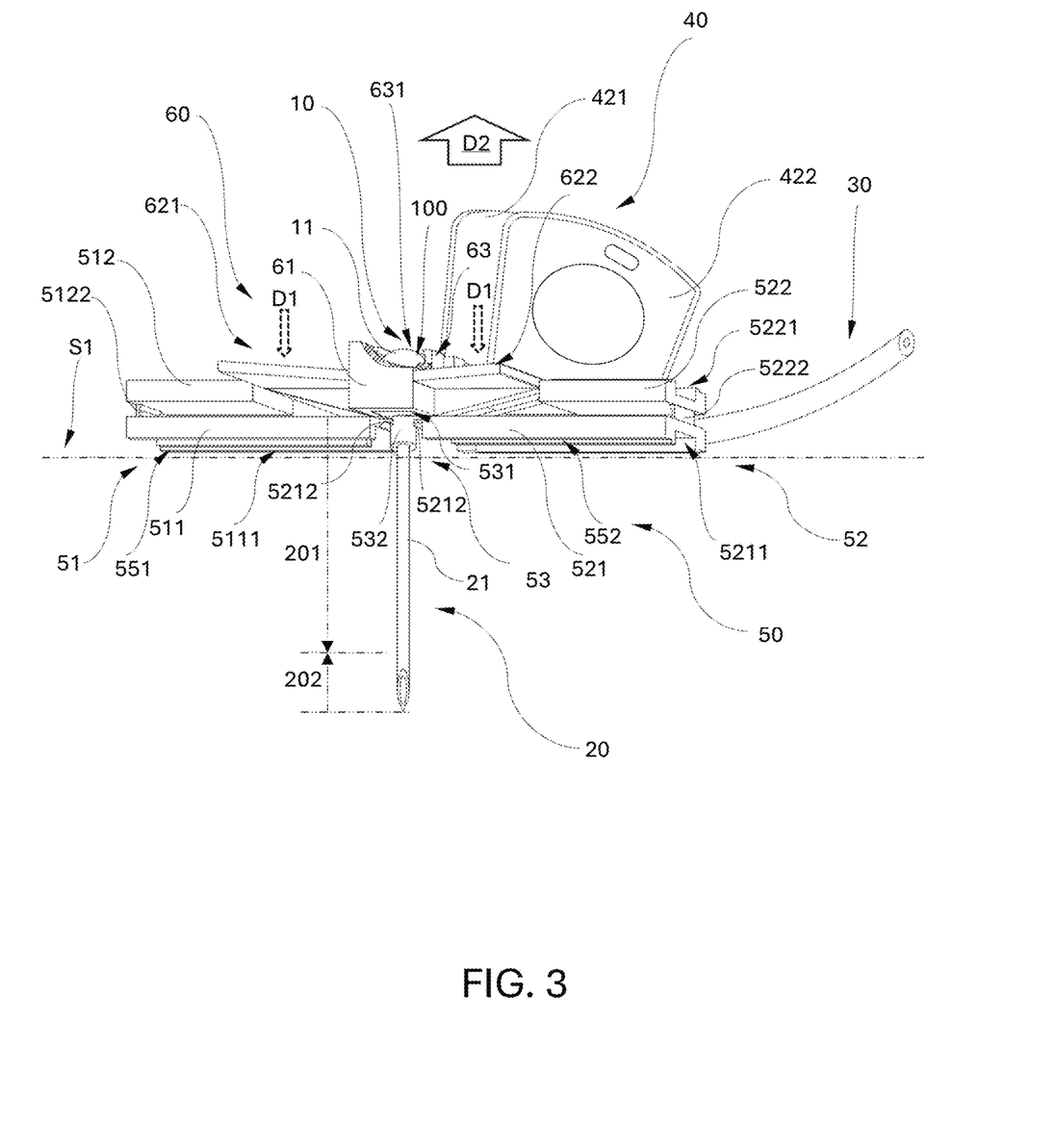
FIG. 3 is a partially sectional perspective view of a safety infusion port needle apparatus, during an operation state, according to a preferred embodiment of the present invention.

Referring to FIG. 3, a safety infusion port needle apparatus according to a preferred embodiment of the present invention is illustrated, wherein the safety infusion port needle apparatus includes a needle base 10, a port needle 20, a medical tubing 30, a handle assembly 40, a needle protector housing 50, and a guiding driver 60.

Referring to FIG. 3 to FIG. 6, the port needle 20 comprises a needle 21 which is formed from a cannula and extended from a needle connecting portion 11 of the needle base 10 through a needle mount 22. The medical tubing 30 is connected to a tubing connecting portion 12 of the needle base 10 and communicated with the port needle 20. The handle assembly 40 is mounted to a front portion of the medical tubing 30 and positioned adjacent to the tubing connecting portion 12 of the needle base 10.

Figure 4:
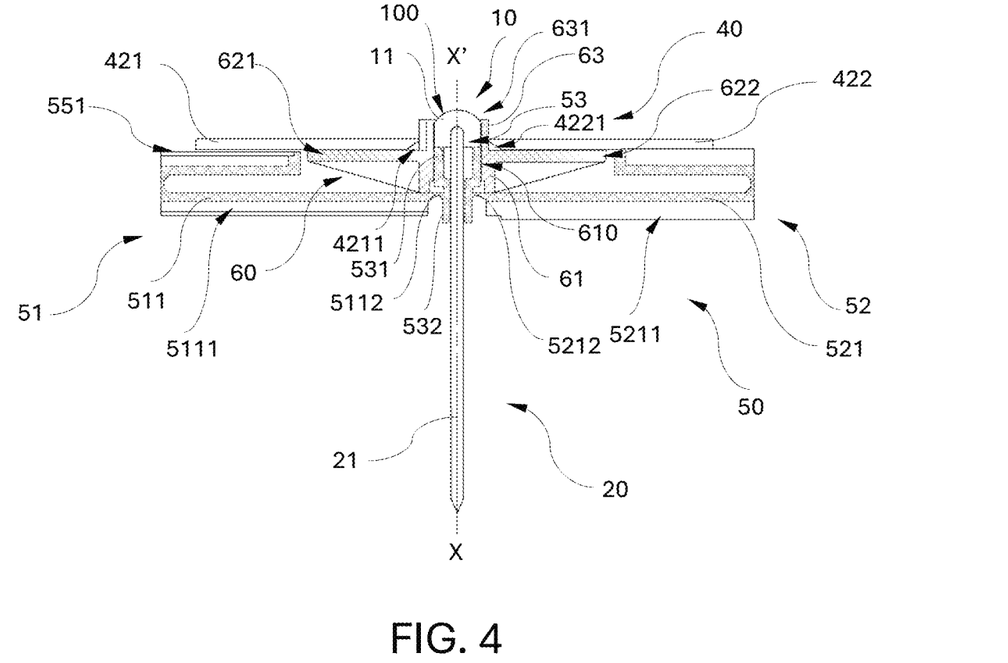
FIG. 4 is a sectional view of the safety infusion port needle apparatus according to the above preferred embodiment of the present invention.
Figure 5:
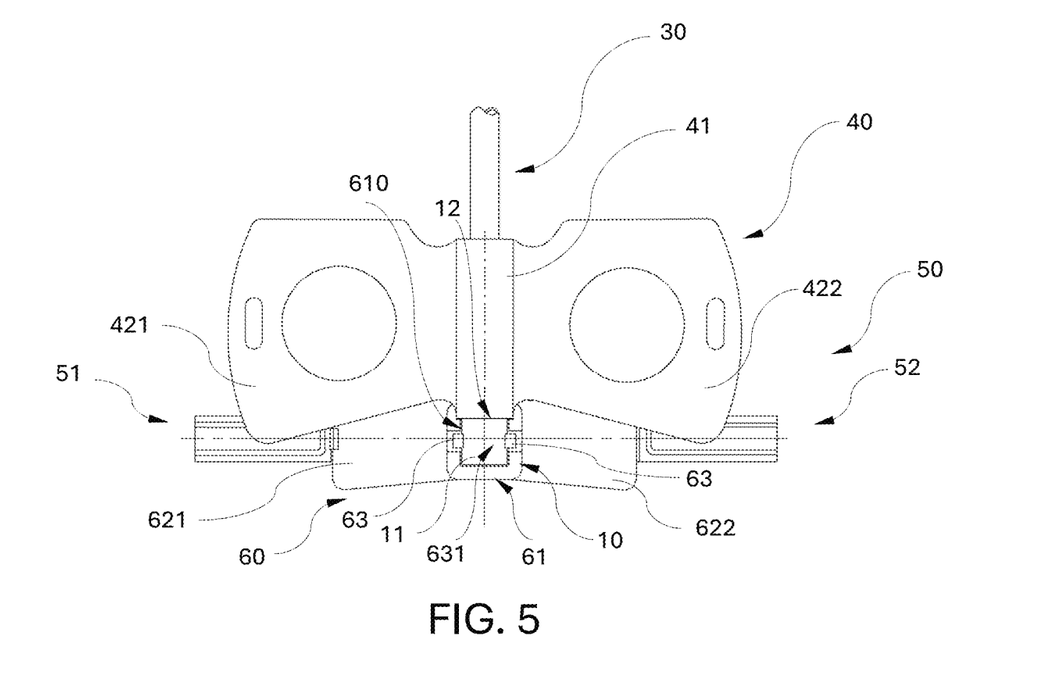
FIG. 5 is a top view of the safety infusion port needle apparatus according to the above preferred embodiment of the present invention.
Figure 6:
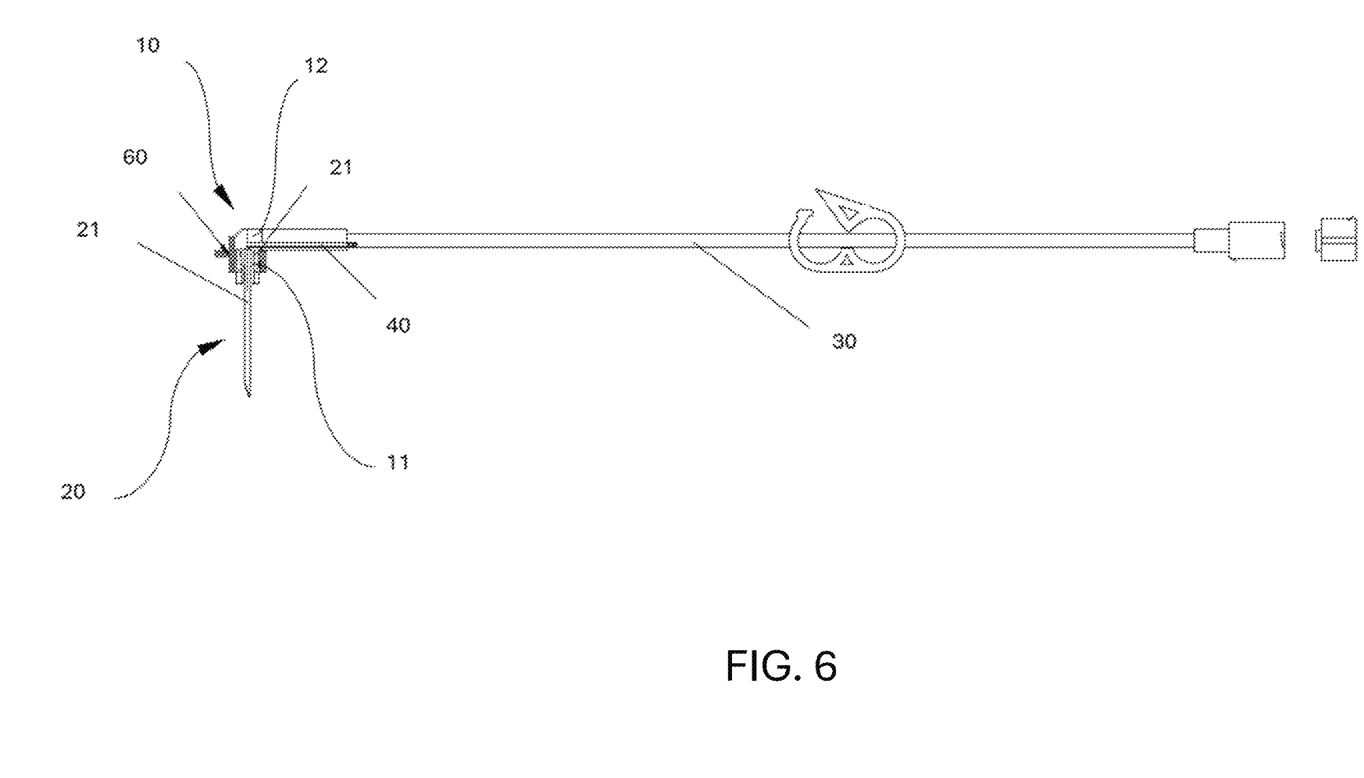
FIG. 6 is a sectional view of the needle base, the port needle and the handle assembly of the safety infusion port needle apparatus according to the above preferred embodiment of the present invention.

Referring to FIG. 3 to FIG. 5, the handle assembly 40 comprises a mounting body 41 mounted to the front portion of the medical tubing and positioned adjacent to the tubing connecting portion 12 of the needle base and a pair of wing handles 421, 422 symmetrically and sidewardly extended from two sides of the mounting body 41 in opposite directions respectively in a pivotal manner. According to the preferred embodiment, as shown in FIG. 4, two pivot slots 4211, 4221, each having a V-shaped cross section, are formed in bottom side of the handle assembly 40 between the two sides of the mounting body 41 and the two wing handles 421, 422 respectively, such that the two wing handles 421, 422 are pivotally connected to the mounting body 41 in lateral positions in such a manner that the operator of the safety infusion port needle apparatus is able to fold the two wing handles 421, 422 upwards from their normal lateral positions as shown in FIG. 5, to upright positions as shown in FIG. 3 to facilitate the operator to use his or her thumb and index finger, for example, of one hand to firmly hold the two upright wing handles 421, 422 of the handle assembly 40 together for applying an upward pulling force thereto to pull up the port needle 20 along an axis X-X' of the port needle 20. After the upfolding force releases, the two wing handles 421, 422 resiliently fold down and return to their lateral positions as shown in FIG. 4 and FIG. 5. With the formation of the two pivot slots 4211, 4221 to provide the pivotal configuration of the two wing handles 421, 422, the handle assembly 40 can be made of an integral body, for example by plastic injection molding that minimizes the material and production cost thereof with desired precision in configuration.

Figure 9:
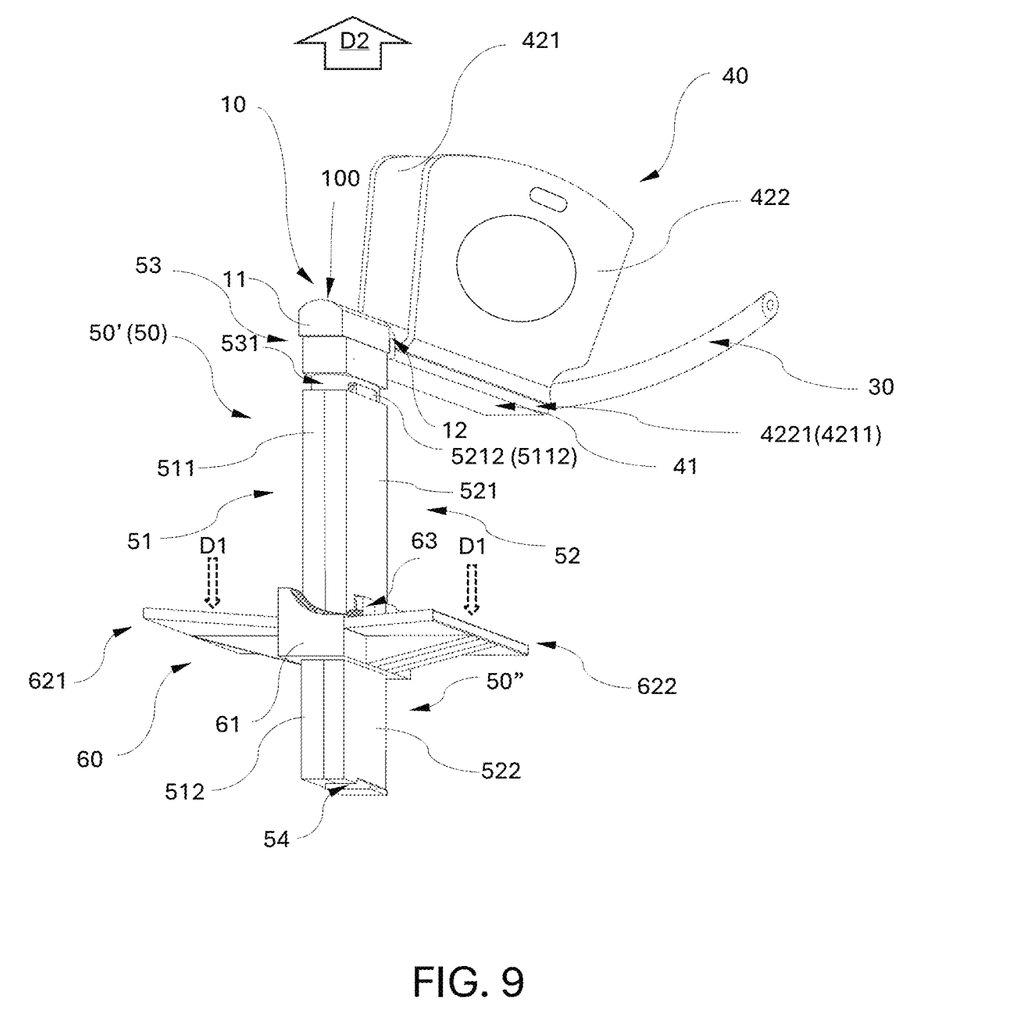
FIG. 9 is a perspective view of the safety infusion port needle apparatus, during an enclosure state, according to a preferred embodiment of the present invention.
Figure 10:
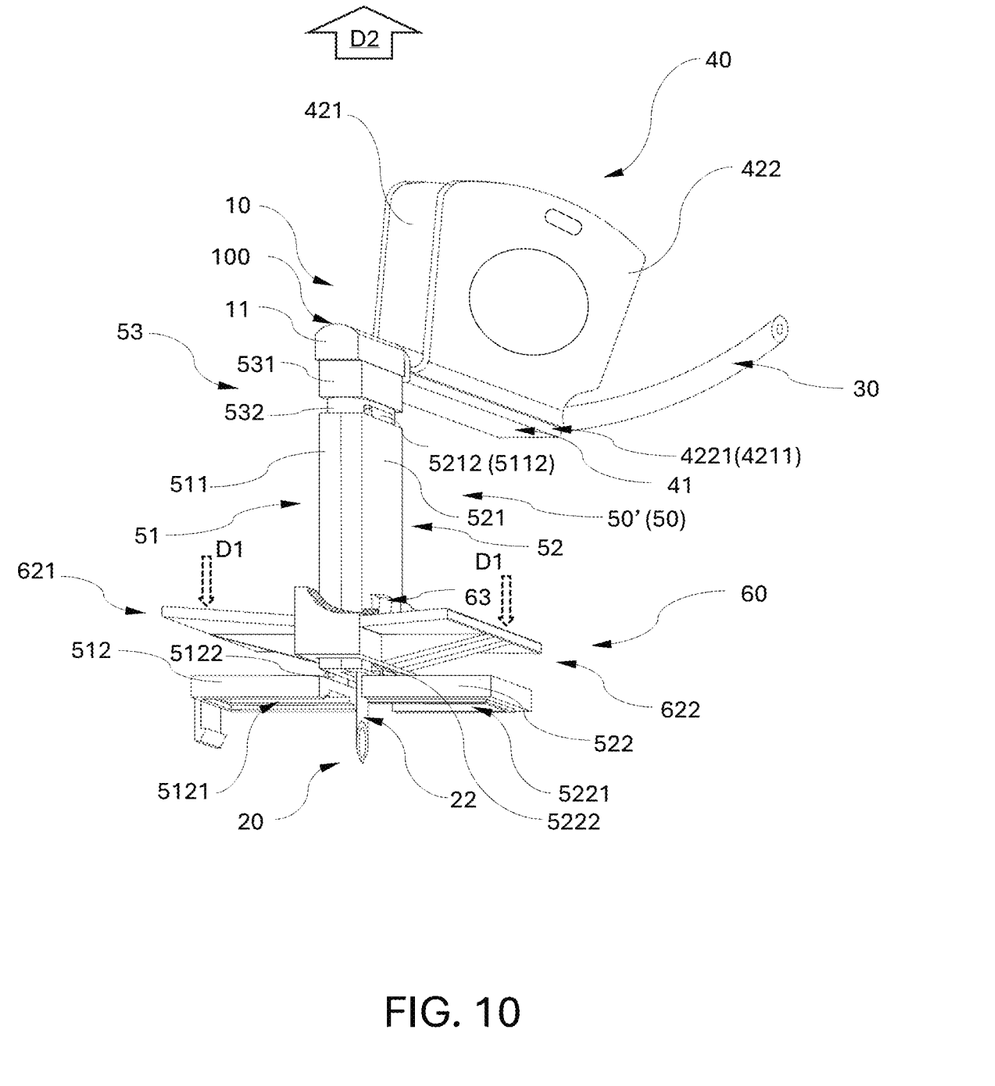
FIG. 10 is a perspective view of the safety infusion port needle apparatus, while converting from the operation state as shown in FIG. 3 to the enclosure state as shown in FIG. 9, according to a preferred embodiment of the present invention.

Referring to FIGS. 3-5, FIGS. 7A-7B and FIGS. 9-10, the needle protector housing 50 includes two enclosure petals 51, 52 pivotally coupled with the needle base 10 and configured to be moved between an operation state that the port needle 20 is exposed for infusion operation, as shown in FIG. 3 and FIG. 4, and an enclosure state that the two enclosure petals 51, 52 are combined together to form a tubular housing 50' to enclose and conceal the port needle 20 therein, as shown in FIG. 10.

According to the preferred embodiment, the housing base 53 has an upper portion 531, preferably having a rectangular shape, and a lower portion 532, preferably having a circular shape, having a size smaller than that of the upper portion 531. The needle protector housing 50 further includes a tubular housing base 53 having an inner diameter equal to an outer diameter of the port needle 20, as shown in FIG. 3 and FIG. 4, such that the housing base 53 is coaxially sleeved and mounted on the upper portion 531 of the port needle 20 and positioned right below the needle connecting portion 11 of the needle base 10.

Referring to FIGS. 3-4 and FIGS. 7A-7B, each of the enclosure petals 51, 52 of the needle protector housing 50 comprises an enclosure shell 511, 521, having a U-shaped cross section, which defines an enclosure groove 5111, 5211 longitudinal extended therethrough and having a width larger than the outer diameter of the port needle 20. The two enclosure shells 511, 521, each having a predetermined housing length, are connected to two opposing sides of the lower portion 532 of the housing base 53 through two pivot hinges 5112, 5212 and extended in opposite directions laterally. Since each of the two pivot hinges 5112, 5212 has a thickness thinner than a thickness of each of the enclosure shells 511, 521, the two enclosure shells 511, 521 are downwardly foldable towards the port needle 20 from their lateral positions as shown in FIG. 3 and FIG. 4, to longitudinal positions, as shown in FIG. 9 and FIG. 10, until the two enclosure shells 511, 521 are combined side by side to form the tubular housing 50' to enclose and conceal the port needle 20, where the two enclosure grooves 5111, 5211 form an elongated enclosure chamber to receive the port needle 20 therein.

Referring to FIG. 3 to FIG. 5 and FIG. 8A to FIG. 8B, the guiding driver 60 comprises a guiding portion 61 and two supporter arm portions 621, 622 symmetrically and integrally extended from two opposing sides of the guiding sleeve portion 63 respectively, wherein the guiding sleeve portion 61 is slidably set on the needle base 10 during the operation state where the needle protector housing 50 is positioned below the guiding driver 60 such that the port needle 20 is able to be inserted and implanted in an access port positioned in a body surface of a patient, and that the guiding sleeve portion 61 is configured to be moved away from the needle base 10 along the port needle 20, when the port needle 20 is driven by the handle assembly 40 to pull out from the access port and body surface of the patent, to drive the two support arms 621, 622 to combine together to form the tubular housing 50' to enclose and conceal the withdrawn port needle 20 therein, so as to fully protect the withdrawn port needle 20 after infusion from being contacted with outside.

Figure 8A:
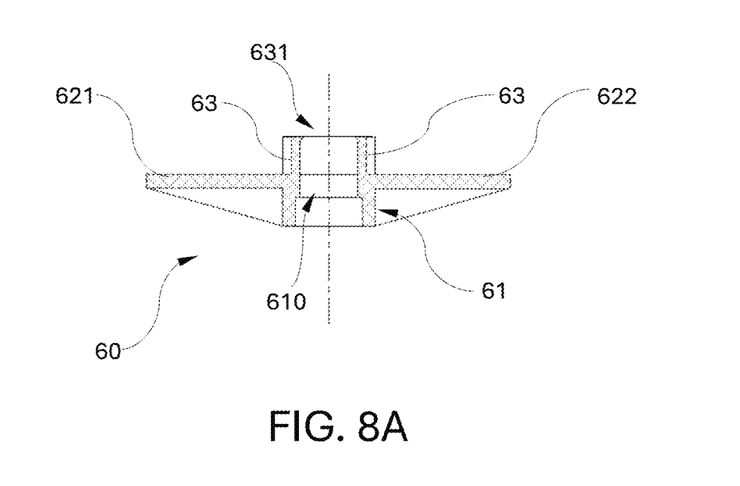
FIG. 8A is a sectional view of the guiding driver of the safety infusion port needle apparatus according to the above preferred embodiment of the present invention.
Figure 8B:
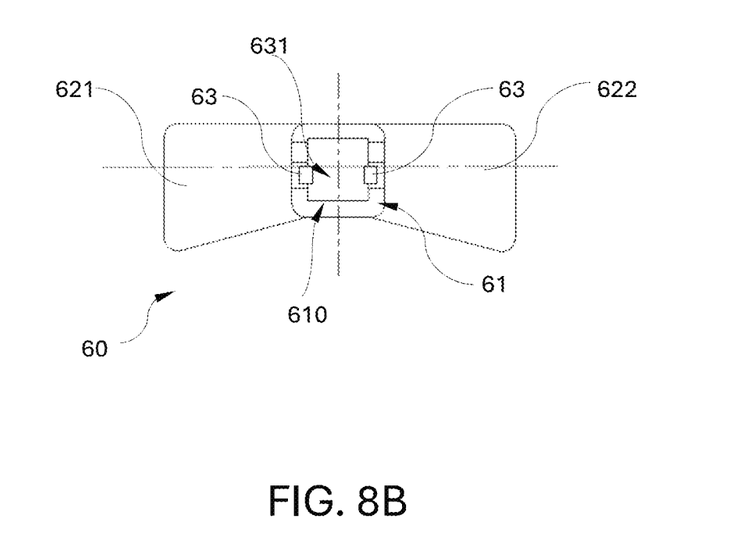
FIG. 8B is a top view of the guiding driver of the safety infusion port needle apparatus according to the above preferred embodiment of the present invention.

According to the preferred embodiment of the present invention, as shown in FIG. 3 to FIG. 5, a top end of the needle base 10 is a convex curved surface 100 and the guiding sleeve portion 61 of the guiding driver 60 has a rectangular guiding hole 610, sized to slidably mounted on the upper portion 531 of the housing base 53, wherein at least a pair of catch members 63 is upwardly extended from two opposing sides of a top end of the guiding sleeve portion 61 to define a catch opening 631 therebetween to communicate the guiding hole 610 with outside, as shown in FIG. 8A, wherein the catch opening 631 has a width slightly smaller than that of the top curved surface 100 of the needle base 10, such that the pair of catch members 63 are resilient arms and hold on the needle base 10 while the guiding sleeve portion 61 is sleeved on the upper portion 531 of the housing base 53 of the needle protector housing 50 and the upper portion 531 is slidably inserted in the guiding hole 610. Accordingly, during the operation state as shown in FIG. 3 to FIG. 5, the guiding driver 60 is mounted on the needle base 10 and positioned between the handle assembly 40 and the needle protector housing 50.

Referring to FIG. 3 to FIG. 5, the pair of wing handles 421, 422 of the handle assembly 40, the pair of supporter arm portions 621, 622 of the guiding driver 60, and the pair of the enclosure shells 511, 521 of the enclosure petals 51, 52 of the needle protector housing 50 are all laterally extended sidewardly with respect to the needle base 10 and the port needle 20 to without blocking the operator's sight while puncturing the port needle 20 in the insertion site of the access port that may include a silicon septum positioned under a body surface S1 of the patient (as shown in FIG. 3).

Therefore, the operator can precisely insert and implant the port needle 20 in the access port positioned into the body surface S1 of the patient. In addition, the withdrawal of the port needle 20 of the safety infusion port needle apparatus of the present invention from the body surface S1 of the patient is easy and precise after the infusion, wherein the guiding sleeve portion 61 is configured to be moved away from the needle base 10 along the port needle 20, when the port needle 20 is driven by the handle assembly 40 to pull out from the access port and body surface S1 of the patent, to drive the two enclosure petals 51, 52 to combine together to form the tubular housing 50' to enclose and conceal the withdrawn port needle 20 therein, so as to fully protect the withdrawn port needle 20 after infusion from being contacted with outside.

During the insertion of the port needle 20, as shown in FIG. 3, the operator may also fold up the two wing handles 421, 422 to their upright positions as a handle for ease gripping with one hand and hold the needle base 10 and guiding driver 60 with another hand to aim and drive the port needle 20 while puncturing insertion site of the access port precisely. After the infusion, a withdrawal process of the port needle 20 includes the steps of:

(a) holding the guiding driver 60 in position and slightly pushing the two supporter arm portions 621, 622 in a first direction D1 (e.g. downwards) towards the body surface S1 of the patient with one hand of the operator so as to maintain the safety infusion port needle apparatus in a steady condition, as shown in FIG. 3;

(b) folding up the two wing handles 421, 422 of the handle assembly 40 to the upright positions thereof, and gripping on the two folded-up wing handles 421, 422 with another hand of the operator and applying a pulling force in a second direction D2 (e.g. upwards), opposing the first direction D1 applied to the guiding driver 60 to hold in position and slightly pushed down in the first direction D1 until the curved surface 100 of the needle base 10 is pulled in the second direction D2 to enlarge the catching opening 631 (i.e. a distance between the two catch members 63) to pull out the needle base 10 from the catch opening 631 of the guiding driver 60 in the second direction D2 (upwardly), so that the port needle 20 is able to be pulled up with the up moving handle assembly 40 to withdraw from the body surface S1 of the patient simultaneously;

(c) at the same time, while the housing base 53 mounted on the port needle 20 is also pulled in the second direction D2 by the up moving handle assembly 40 until the two enclosure shells 511, 521 of the needle protector housing 50 meet a bottom surface of the guiding sleeve portion 61 of the guiding driver 60, the continuous pulling up of the housing base 53 of the needle protector housing 50 and the port needle 20 in the second direction D2 through the handle assembly 40 drives the two enclosure shells 511, 521 of the two enclosure petals 51, 52 of the needle protector housing 50 to be pressed down in the first direction D1 by the bottom surface of the guiding sleeve portion 61 of the guiding driver 60 (which is held in position by one hand of the operator) to relatively and pivotally fold down towards each other by folding up the two pivot hinges 5112, 5212 to pass through the rectangular guiding hole 610; and (d) continuously up pulling the handle assembly 40 in the second direction D2 to drive and withdraw the port needle 20 substantially drives the two enclosure shells 511, 521 to pass through the guiding hole 610 and, relatively, the guiding driver 60 also drives the two enclosure shells 511, 521 to pass through the guiding hole 610 and be completely combined together to form the tubular housing 50', as shown in FIG. 9 and FIG. 10, to enclose and conceal the withdrawn port needle 20 therein, so as to fully protect the withdrawn port needle 20 after infusion from being contacted with outside.

It is appreciated that the guiding driver 60 also functions as a holder to lock the two combined enclosure shells 511, 521 of the two enclosure petals 51, 52 of the needle protector housing 50 in the tubular housing 50' (enclosure state) to enclose and protect the withdrawn port needle 20 from being contacted outside.

Referring to FIG. 3 to FIG. 5, FIG. 7A to FIG. 7B, and FIG. 9 to FIG. 10, according to the preferred embodiment of the present invention, in order to provide better accessibility of the port needle 20 when a longer port needle 20 is used for puncturing the port needle 20 in the insertion site of the access port, the two enclosure petals 51, 52 of the needle protector housing 50 are made into two sections, wherein the first section of each of the two enclosure petals 51, 52 is the enclosure shell 511, 521 and the section of each of the two enclosure petals 51, 52 for enclosing and concealing a main portion 201 of the port needle 20 is an enclosure cover 512, 522 to enclose and conceal an end portion 202 of the port needle 20, as shown in FIG. 3.

Figure 7A:
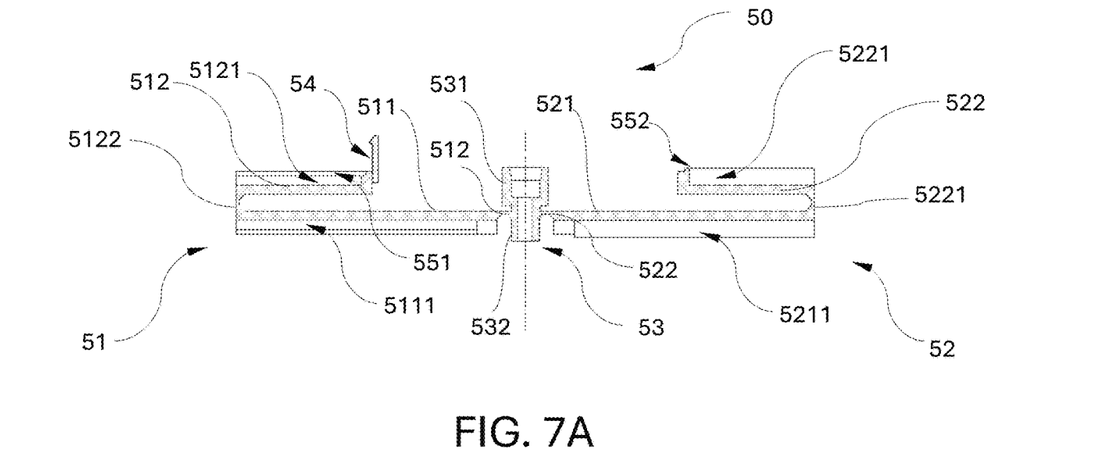
FIG. 7A is a sectional view of the needle protector housing of the safety infusion port needle apparatus according to the above preferred embodiment of the present invention.
Figure 7B:
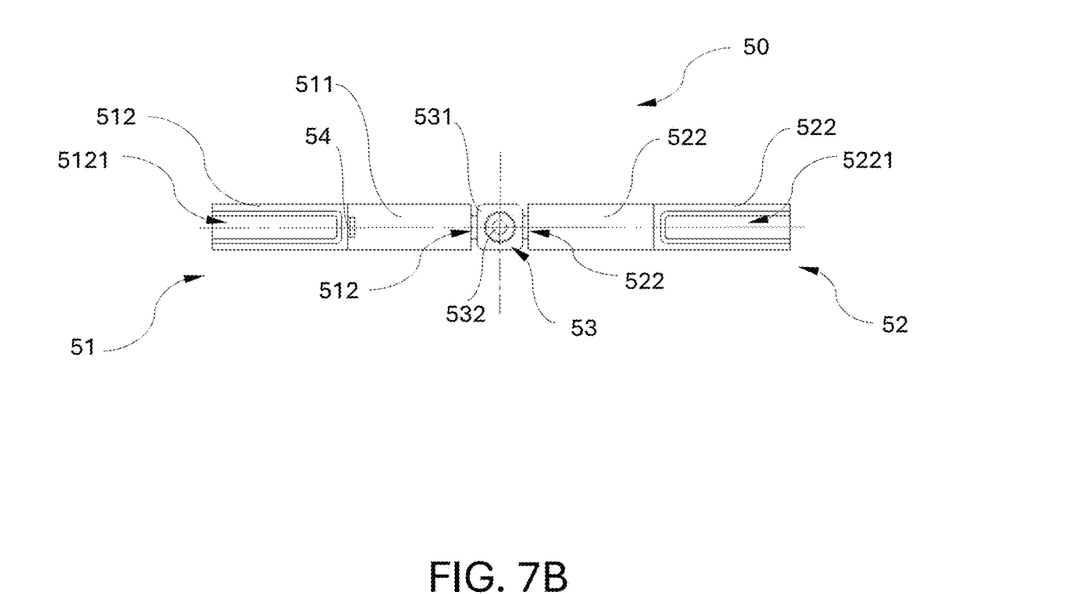
FIG. 7B is a top view of the needle protector housing of the safety infusion port needle apparatus according to the above preferred embodiment of the present invention.

As shown in FIG. 7A and FIG. 7B, each of the two enclosure covers 512, 522 has a shorter length than that of the corresponding enclosure shell 511, 521 and a U-shaped cross section like the corresponding enclosure shell 511, 521 to define a second enclosure groove 5121, 5221 therein. Each of the enclosure petals 51, 52 further comprises a second pivot hinge 5122, 5222 pivotally connecting the enclosure cover 512, 522 to a distal end of the corresponding enclosure shell 511, 521 in such a manner that the two enclosure covers 512, 522 are normally overlapped on top of the two enclosure shells 511, 521 respectively during the operation state, as shown in FIG. 3. According to the folding configuration of the two enclosure shells 511, 521 and the two enclosure covers 521, 522 of the two enclosure petals 51, 52, the normal lengths of the two enclosure petals 51, 52 are shortened to provide better accessibility of the port needle 20 to the operator during insertion of the port needle 20.

In addition, as shown in FIG. 10, when the handle assembly 40 and the needle base 10 are pulling up in the second direction D2, the guiding driver 60 first guides and drives the two enclosure shells 511, 521 towards each other to combine to form the tubular housing 50' to enclose and conceal the main portion 201 of the port needle 20. Then, as shown in FIG. 9, the continuous pulling of the handle assembly 40 and the needle base 10 in the second direction D2 also drives the two enclosure covers 512, 522 towards each other by folding up the two second pivot hinges 5122, 5222 to form a needle end tubular housing 50" to enclose and conceal the end portion 202 of the port needle 20 therein.

According to the preferred embodiment of the present invention, referring to FIG. 7A and FIG. 7B, the needle protector housing further comprises a locker member 54 integrally connected to a distal end of one of the two enclosure covers 512, 522, which is configured to engage with a distal end of the other one of the two enclosure covers 512, 522 when the two enclosure covers 512, 522 are guided and driven by the guiding driver 60 to combine together, during the withdrawal of the port needle 20 by pulling the handle assembly 40 in the second direction D2, to form the second tubular housing 50", as shown in FIG. 9, so as to lock up an enclosure state of the needle protector housing 50 to fully conceal the withdrawn port needle 20 therein, even though the enclosed needle protector housing 50 is completely pulled away and separated from the guiding driver 60.

It is further worth mentioning that, in order to better guide and align the pair of two enclosure shells 511, 512 and the pair of two enclosure covers 512, 522 to combine together side by side, as shown in FIG. 3 and FIG. 7A, alignment recess 551 and rim 552 are respectively form in side edges of the two enclosure shells 511, 512 and the two enclosure covers 512, 522, such that when the two enclosure shells 511, 521 as well as the two enclosure covers 512, 522 are guided and driven towards each other and combine together, the corresponding pairs of recess 551 and rim 552 are aligned and engaged with each other.

In view of above, the safety infusion port needle apparatus substantially solves the drawbacks of the conventional port needle apparatus by providing the needle protector housing 50 and the relative movement of the guiding driver 60 and the needle protector housing 50 with respect to the pulling of the handle assembly 40. The entire withdrawn port needle 20 can be enclosed and concealed by the combined needle protector housing 50. In addition, during the operation state, the handle assembly 40, the needle protector housing 50 and the guiding driver 60 are arranged sidewards to ensure the operator of the safety infusion port needle apparatus can access the port needle 20 for precise insertion with respect to the body surface S1 of the patient.

Further, the two supporter arm portions 621, 622 of the guiding driver 60 not only reinforce the positioning of the guiding sleeve portion 61, but also provides a stabilizing platform for the operator to stabilize a relative position of the port needle 20 with respect to the access port and the body surface S1 of the patient, such that when the operator applies a pulling force to the handle assembly 40 to withdraw the port needle 20, the operator is able to also apply a supporting force in an opposite direction D2 on the two supporter arm portions 621, 622. Therefore, the guiding sleeve portion 61 correspondingly guides the two enclosure petals 51, 52 of the needle protector housing 50 to move towards each other until being combined to form the tubular housing 50' while the needle base 10 is pulling away from the guiding driver 60, wherein the combining and forming of the tubular housing 50' of the two enclosure petals 51, 52 by means of the guiding sleeve portion 61 of the guiding driver 60 also significantly guide the withdrawal of the port needle 20 in a stable and precise manner to prevent accidently injury to the body tissue or vessel of the patient during the withdrawal of the port needle 20.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and are subject to change without departure from such principles. Therefore, this invention includes all modifications encompassed within the spirit and scope of the following claims.

What is claimed is:

1. A safety infusion port needle apparatus, including:
   a needle base;
   a port needle extended from a needle connecting portion of said needle base;
   a medical tubing connected to a tubing connecting portion of said needle base in communication with said port needle;
   a handle assembly mounted to said medical tubing and positioned adjacent to said tubing connecting portion of said needle base;
   a needle protector housing including two enclosure petals pivotally coupled with said needle base and configured to be moved between an operation state that said port needle is exposed for infusion operation and an enclosure state that said two enclosure petals are combined together to form a tubular housing to enclose and conceal said port needle therein; and
   a guiding driver comprising a guiding sleeve portion and two supporter arm portions symmetrically extended from two opposing sides of said guiding sleeve portion respectively, wherein said guiding sleeve portion is slidably set on said needle base during the operation state where said needle protector housing is positioned below said guiding driver such that said port needle is able to be inserted and implanted in an access port positioned in a body surface of a patient, and that said guiding sleeve portion is configured to be moved away from said needle base along said port needle, when said port needle is driven by said handle assembly to pull out from the access port and the body surface of the patent, to drive said two enclosure petals to combine together to form said tubular housing to enclose and conceal said withdrawn port needle therein, so as to fully protect said withdrawn port needle after infusion.

2. The safety infusion port needle apparatus, as recited in claim 1, wherein, during the operation state, said handle assembly, said needle protector housing and said guiding driver are arranged sidewards to ensure the operator of the safety infusion port needle apparatus being able to access said port needle for precise insertion with respect to the body surface of the patient.

3. The safety infusion port needle apparatus, as recited in claim 1, wherein said needle protector housing further comprises a tubular housing base having an upper portion, a lower portion and an inner diameter equal to an outer diameter of said port needle, such that said tubular housing base is coaxially sleeved and mounted on said upper portion of said port needle and positioned right below said needle connecting portion of said needle base, wherein said guiding driver has a guiding hole sized to slidably mounted on said upper portion of said tubular housing base.

4. The safety infusion port needle apparatus, as recited in claim 3, wherein at least a pair of catch members is upwardly extended from two opposing sides of a top end of said guiding sleeve portion to define a catch opening therebetween, wherein said catch opening has a width slightly smaller than that of a top curved surface of said needle base, such that said pair of catch members hold on said needle base while said guiding sleeve portion is sleeved on said upper portion of said tubular housing base of said needle protector housing and said upper portion is slidably inserted in the guiding hole, thereby, during the operation state, said guiding driver is mounted on said needle base and positioned between said handle assembly and said needle protector housing.

5. The safety infusion port needle apparatus, as recited in claim 4, wherein each of said enclosure petals of said needle protector housing comprises an enclosure shell, having a U-shaped cross section, which defines an enclosure groove longitudinally extended therethrough and having a width larger than said outer diameter of said port needle, wherein said two enclosure shells, each having a predetermined housing length, are connected to two opposing sides of said lower portion of said housing base through two pivot hinges and extended in opposite directions laterally, such that said two enclosure shells are downwardly foldable towards said port needle from lateral positions thereof to longitudinal positions, until said two enclosure shells are combined side by side to form said tubular housing to enclose and conceal said port needle, where said two enclosure grooves form an elongated enclosure chamber to receive said port needle therein.

6. The safety infusion port needle apparatus, as recited in claim 5, wherein each of said two pivot hinges has a thickness thinner than a thickness of each of said enclosure shells.

7. The safety infusion port needle apparatus, as recited in claim 6, wherein said handle assembly comprises a mounting body and two wing handles symmetrically and sidewardly extended from two sides of said mounting body in opposite directions respectively in a pivotal manner, wherein said mounting body is mounted adjacent to said tubing connecting portion of said needle base, wherein said two wing handles are configured to be able to be folded upwards to upright positions for facilitating an operator to hold said two wing handles together with one hand for applying a pulling force in a first direction to pull said port needle for an upward movement while said guiding driver is held in position and slightly push in a second direction, opposing to the first direction, by another hand until said need base is pulled out from said guiding driver in the first direction, wherein while said tubular housing base mounted on said port needle is pulled in the first direction by the upward movement of said handle assembly until said two enclosure shells of said needle protector housing meet said guiding sleeve portion of said guiding driver, a continuous pulling of said housing base of said needle protector housing and said port needle in the first direction through said handle assembly drives said two enclosure shells of said two enclosure petals of said needle protector housing to be pressed down in the second direction by said guiding sleeve portion of said guiding driver to relatively and pivotally fold down towards each other to pass through said guiding hole until said two enclosure shells are driven by said guiding driver to be completely combined together to form said tubular housing where said two enclosure grooves form said enclosure chamber to enclose and conceal said port needle therein.

8. The safety infusion port needle apparatus, as recited in claim 7, wherein two pivot slots, each having a v-shaped cross section, are formed in a bottom side of the handle assembly and positioned between two sides of said mounting body and said two wing handles respectively, such that said two wing handles are pivotally connected to said mounting body in lateral positions in such a manner that said two wing handles are able to be folded up at said two pivot slots respectively to the upright positions thereof, wherein when a holding of said two wing handles is released, said two wing handles resiliently fold down and return to the lateral positions thereof.

9. The safety infusion port needle apparatus, as recited in claim 5, wherein said handle assembly comprises a mounting body and two wing handles symmetrically and sidewardly extended from two sides of said mounting body in opposite directions respectively in a pivotal manner, wherein said mounting body is mounted adjacent to said tubing connecting portion of said needle base, wherein said two wing handles are configured to be able to be folded upwards to upright positions for facilitating an operator to hold said two wing handles together with one hand for applying a pulling force in a first direction to pull said port needle for an upward movement while said guiding driver is held in position and slightly push in a second direction, opposing to the first direction, by another hand until said need base is pulled out from said guiding driver in the first direction, wherein while said tubular housing base mounted on said port needle is pulled in the first direction by the upward movement of said handle assembly until said two enclosure shells of said needle protector housing meet said guiding sleeve portion of said guiding driver, a continuous pulling of said housing base of said needle protector housing and said port needle in the first direction through said handle assembly drives said two enclosure shells of said two enclosure petals of said needle protector housing to be pressed down in the second direction by said guiding sleeve portion of said guiding driver to relatively and pivotally fold down towards each other to pass through said guiding hole until said two enclosure shells are driven by said guiding driver to be completely combined together to form said tubular housing where said two enclosure grooves form said enclosure chamber to enclose and conceal said port needle therein.

10. The safety infusion port needle apparatus, as recited in claim 5, wherein each of said two enclosure petal further comprises an enclosure cover, which has a length shorter than that of said enclosure shell of said each of said two enclosure petals and a U-shaped cross section to define a second enclosure groove therein, and a second pivot hinge pivotally connecting said enclosure cover to a distal end of said enclosure shell of said each of said two enclosure petals, wherein said two enclosure covers are normally overlapped on top of said two enclosure covers of said two enclosure petals respectively during the operation state, wherein during the enclosure state while said handle assembly and said needle base are pulling in the first direction, wherein said guiding driver, which has guided and driven said two enclosure shells towards each other to combine to form said tubular housing, also drives said two enclosure covers towards each other by folding up said two second pivot hinges to form a needle end tubular housing to enclose and conceal an end portion of said port needle therein.

11. The safety infusion port needle apparatus, as recited in claim 3, wherein each of said enclosure petals of said needle protector housing comprises an enclosure shell, having a U-shaped cross section, which defines an enclosure groove longitudinally extended therethrough and having a width larger than said outer diameter of said port needle, wherein said two enclosure shells, each having a predetermined housing length, are connected to two opposing sides of said lower portion of said housing base through two pivot hinges and extended in opposite directions laterally, wherein each of said two pivot hinges has a thickness thinner than a thickness of each of said enclosure shells, such that said two enclosure shells are downwardly foldable towards said port needle from lateral positions thereof to longitudinal positions, until said two enclosure shells are combined side by side to form said tubular housing to enclose and conceal said port needle, where said two enclosure grooves form an elongated enclosure chamber to receive said port needle therein.

12. The safety infusion port needle apparatus, as recited in claim 11, wherein each of said two pivot hinges has a thickness thinner than a thickness of each of said enclosure shells.

13. The safety infusion port needle apparatus, as recited in claim 12, wherein said handle assembly comprises a mounting body and two wing handles symmetrically and sidewardly extended from two sides of said mounting body in opposite directions respectively in a pivotal manner, wherein said mounting body is mounted adjacent to said tubing connecting portion of said needle base, wherein said two wing handles are configured to be able to be folded upwards to upright positions for facilitating an operator to hold said two wing handles together with one hand for applying a pulling force in a first direction to pull said port needle for an upward movement while said guiding driver is held in position and slightly push in a second direction, opposing to the first direction, by another hand until said need base is pulled out from said guiding driver in the first direction, wherein while said tubular housing base mounted on said port needle is pulled in the first direction by the upward movement of said handle assembly until said two enclosure shells of said needle protector housing meet said guiding sleeve portion of said guiding driver, a continuous pulling of said housing base of said needle protector housing and said port needle in the first direction through said handle assembly drives said two enclosure shells of said two enclosure petals of said needle protector housing to be pressed down in the second direction by said guiding sleeve portion of said guiding driver to relatively and pivotally fold down towards each other to pass through said guiding hole until said two enclosure shells are driven by said guiding driver to be completely combined together to form said tubular housing where said two enclosure grooves form said enclosure chamber to enclose and conceal said port needle therein.

14. The safety infusion port needle apparatus, as recited in claim 13, wherein two pivot slots, each having a v-shaped cross section, are formed in a bottom side of the handle assembly and positioned between two sides of said mounting body and said two wing handles respectively, such that said two wing handles are pivotally connected to said mounting body in lateral positions in such a manner that said two wing handles are able to be folded up at said two pivot slots respectively to the upright positions thereof, wherein when a holding of said two wing handles is released, said two wing handles resiliently fold down and return to the lateral positions thereof.

15. The safety infusion port needle apparatus, as recited in claim 14, wherein each of said two enclosure petal further comprises an enclosure cover, which has a length shorter than that of said enclosure shell of said each of said two enclosure petals and a U-shaped cross section to define a second enclosure groove therein, and a second pivot hinge pivotally connecting said enclosure cover to a distal end of said enclosure shell of said each of said two enclosure petals, wherein said two enclosure covers are normally overlapped on top of said two enclosure covers of said two enclosure petals respectively during the operation state, wherein during the enclosure state while said handle assembly and said needle base are pulling in the first direction, wherein said guiding driver, which has guided and driven said two enclosure shells towards each other to combine to form said tubular housing, also drives said two enclosure covers towards each other by folding up said two second pivot hinges to form a needle end tubular housing to enclose and conceal an end portion of said port needle therein.

16. The safety infusion port needle apparatus, as recited in claim 13, wherein each of said two enclosure petal further comprises an enclosure cover, which has a length shorter than that of said enclosure shell of said each of said two enclosure petals and a U-shaped cross section to define a second enclosure groove therein, and a second pivot hinge pivotally connecting said enclosure cover to a distal end of said enclosure shell of said each of said two enclosure petals, wherein said two enclosure covers are normally overlapped on top of said two enclosure covers of said two enclosure petals respectively during the operation state, wherein during the enclosure state while said handle assembly and said needle base are pulling in the first direction, wherein said guiding driver, which has guided and driven said two enclosure shells towards each other to combine to form said tubular housing, also drives said two enclosure covers towards each other by folding up said two second pivot hinges to form a needle end tubular housing to enclose and conceal an end portion of said port needle therein.

17. The safety infusion port needle apparatus, as recited in claim 12, wherein each of said two enclosure petal further comprises an enclosure cover, which has a length shorter than that of said enclosure shell of said each of said two enclosure petals and a U-shaped cross section to define a second enclosure groove therein, and a second pivot hinge pivotally connecting said enclosure cover to a distal end of said enclosure shell of said each of said two enclosure petals, wherein said two enclosure covers are normally overlapped on top of said two enclosure covers of said two enclosure petals respectively during the operation state, wherein during the enclosure state while said handle assembly and said needle base are pulling in the first direction, wherein said guiding driver, which has guided and driven said two enclosure shells towards each other to combine to form said tubular housing, also drives said two enclosure covers towards each other by folding up said two second pivot hinges to form a needle end tubular housing to enclose and conceal an end portion of said port needle therein.

18. The safety infusion port needle apparatus, as recited in claim 11, wherein said handle assembly comprises a mounting body and two wing handles symmetrically and sidewardly extended from two sides of said mounting body in opposite directions respectively in a pivotal manner, wherein said mounting body is mounted adjacent to said tubing connecting portion of said needle base, wherein said two wing handles are configured to be able to be folded upwards to upright positions for facilitating an operator to hold said two wing handles together with one hand for applying a pulling force in a first direction to pull said port needle for an upward movement while said guiding driver is held in position and slightly push in a second direction, opposing to the first direction, by another hand until said need base is pulled out from said guiding driver in the first direction, wherein while said tubular housing base mounted on said port needle is pulled in the first direction by the upward movement of said handle assembly until said two enclosure shells of said needle protector housing meet said guiding sleeve portion of said guiding driver, a continuous pulling of said housing base of said needle protector housing and said port needle in the first direction through said handle assembly drives said two enclosure shells of said two enclosure petals of said needle protector housing to be pressed down in the second direction by said guiding sleeve portion of said guiding driver to relatively and pivotally fold down towards each other to pass through said guiding hole until said two enclosure shells are driven by said guiding driver to be completely combined together to form said tubular housing where said two enclosure grooves form said enclosure chamber to enclose and conceal said port needle therein.

19. The safety infusion port needle apparatus, as recited in claim 18, wherein each of said two enclosure petal further comprises an enclosure cover, which has a length shorter than that of said enclosure shell of said each of said two enclosure petals and a U-shaped cross section to define a second enclosure groove therein, and a second pivot hinge pivotally connecting said enclosure cover to a distal end of said enclosure shell of said each of said two enclosure petals, wherein said two enclosure covers are normally overlapped on top of said two enclosure covers of said two enclosure petals respectively during the operation state, wherein during the enclosure state while said handle assembly and said needle base are pulling in the first direction, wherein said guiding driver, which has guided and driven said two enclosure shells towards each other to combine to form said tubular housing, also drives said two enclosure covers towards each other by folding up said two second pivot hinges to form a needle end tubular housing to enclose and conceal an end portion of said port needle therein.

20. The safety infusion port needle apparatus, as recited in claim 11, wherein each of said two enclosure petal further comprises an enclosure cover, which has a length shorter than that of said enclosure shell of said each of said two enclosure petals and a U-shaped cross section to define a second enclosure groove therein, and a second pivot hinge pivotally connecting said enclosure cover to a distal end of said enclosure shell of said each of said two enclosure petals, wherein said two enclosure covers are normally overlapped on top of said two enclosure covers of said two enclosure petals respectively during the operation state, wherein during the enclosure state while said handle assembly and said needle base are pulling in the first direction, wherein said guiding driver, which has guided and driven said two enclosure shells towards each other to combine to form said tubular housing, also drives said two enclosure covers towards each other by folding up said two second pivot hinges to form a needle end tubular housing to enclose and conceal an end portion of said port needle therein.

* * * * *